United States Patent
Cronin et al.

(10) Patent No.: US 10,842,390 B2
(45) Date of Patent: Nov. 24, 2020

(54) METHODS, SYSTEMS, AND WEARABLE APPARATUS FOR OBTAINING MULTIPLE HEALTH PARAMETERS

(71) Applicant: KONINKLIJKE PHILIPS N.V., Eindhoven (NL)

(72) Inventors: John Cronin, Bonita Springs, FL (US); Joseph George Bodkin, Fort Meyers, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 40 days.

(21) Appl. No.: 15/547,548

(22) PCT Filed: Feb. 3, 2016

(86) PCT No.: PCT/EP2016/052214
§ 371 (c)(1),
(2) Date: Jul. 31, 2017

(87) PCT Pub. No.: WO2016/124616
PCT Pub. Date: Aug. 11, 2016

(65) Prior Publication Data
US 2018/0263510 A1    Sep. 20, 2018

Related U.S. Application Data

(60) Provisional application No. 62/111,431, filed on Feb. 3, 2015.

(51) Int. Cl.
*A61B 5/0205*    (2006.01)
*A61B 5/00*    (2006.01)
(Continued)

(52) U.S. Cl.
CPC .......... *A61B 5/02055* (2013.01); *A61B 5/002* (2013.01); *A61B 5/0002* (2013.01);
(Continued)

(58) Field of Classification Search
CPC .............. A61B 5/0205; A61B 5/05055; A61B 5/02438; A61B 5/6801; A61B 5/681;
(Continued)

(56) References Cited

U.S. PATENT DOCUMENTS

2012/0059280 A1    3/2012    Horii
2013/0331664 A1*   12/2013   Gilad-Gilor ............ G06F 19/00
                                                    600/301

FOREIGN PATENT DOCUMENTS

CA    2877282 A1    12/2013
CN    103300824 A    9/2013
(Continued)

*Primary Examiner* — Tammie K Marlen

(57) ABSTRACT

The present invention includes systems and methods directed towards a wearable device (100, 200) that can measure health parameters in two levels. The wearable device can measure a health parameter of a user using an attached sensor (112). This sensor measurement is checked against a threshold database (126, 146, 156) that details an action to be taken if the sensor measurement satisfies a health threshold. The health can be predetermined by the user or by a professional. This action can be a request to the user of the wearable device to move the wearable device to another part of his/her body so that the wearable device can gather a second sensor measurement that can provide more detail or context for the first sensor measurement. The wearable device can thus provide two levels of sensor data measurement, which it can store and synchronize to storage on a network/cloud service (104) or to another electronic device (102).

15 Claims, 10 Drawing Sheets

(51) Int. Cl.
*G06F 19/00* (2018.01)
*G16H 40/63* (2018.01)
*G16H 50/30* (2018.01)
*G16H 50/20* (2018.01)
*A61B 5/01* (2006.01)
*A61B 5/024* (2006.01)
*A61B 5/145* (2006.01)

(52) U.S. Cl.
CPC ............ *A61B 5/0006* (2013.01); *A61B 5/486* (2013.01); *A61B 5/681* (2013.01); *A61B 5/742* (2013.01); *A61B 5/7405* (2013.01); *A61B 5/7455* (2013.01); *G06F 19/3418* (2013.01); *G16H 40/63* (2018.01); *G16H 50/30* (2018.01); *A61B 5/01* (2013.01); *A61B 5/02438* (2013.01); *A61B 5/14532* (2013.01); *G16H 50/20* (2018.01)

(58) Field of Classification Search
CPC ...... A61B 5/6802; A61B 5/6824–6829; A61B 5/14532
See application file for complete search history.

(56) References Cited

FOREIGN PATENT DOCUMENTS

| | | |
|---|---|---|
| RU | 2224457 C2 | 2/2004 |
| WO | 2012111012 A1 | 8/2012 |

\* cited by examiner

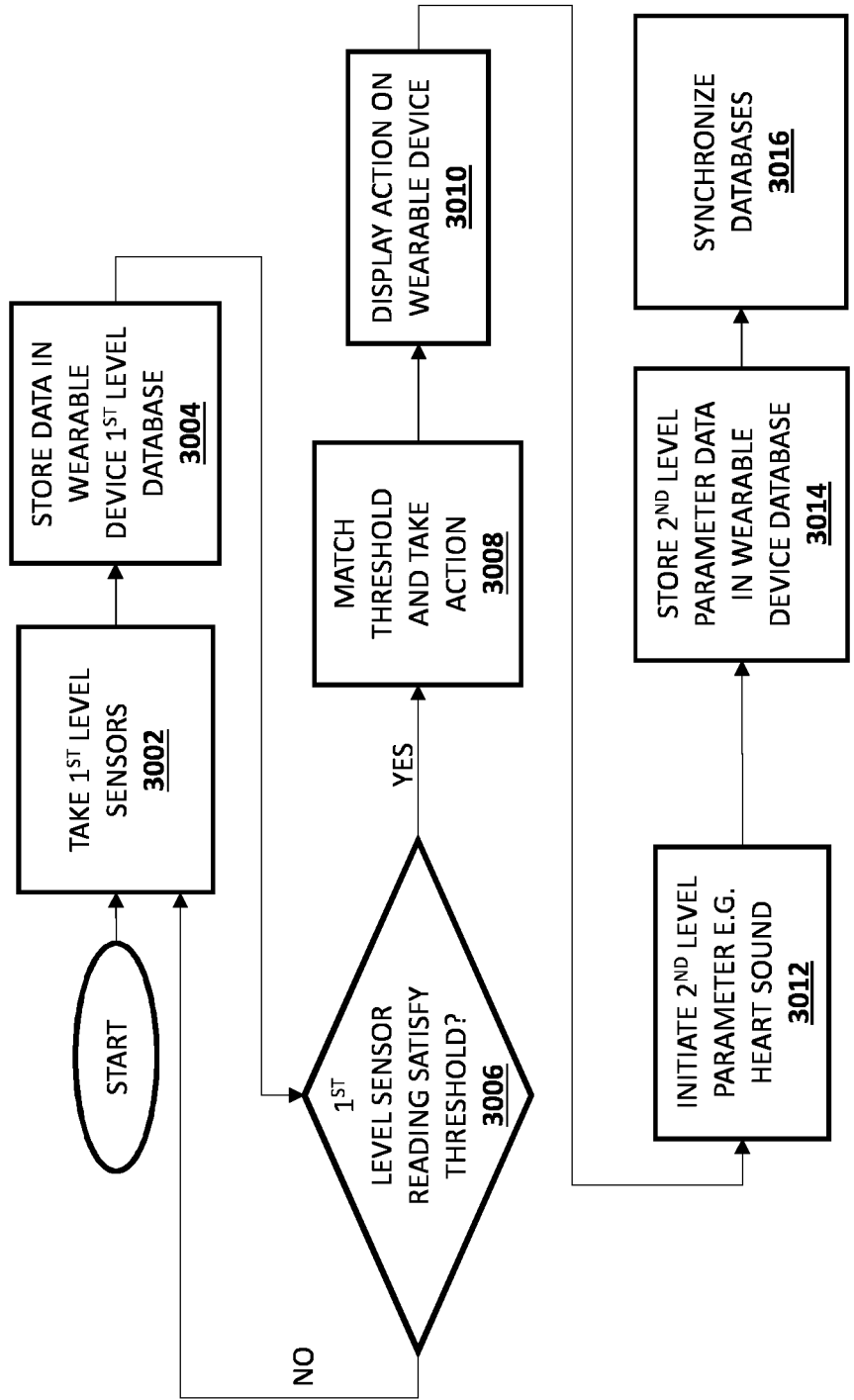

Two Level Wearable Device 1st Level Database

| Date | Time | Pulse | Temperature | Respiratory Rate |
|---|---|---|---|---|
| 12/1/2014 | 9:00AM | 85 | 98 | 12/min |
| 12/1/2014 | 9:05AM | 81 | 99 | 15/min |
| 12/1/2014 | 9:10AM | 90 | 98 | 14/min |
| 12/1/2014 | 9:15AM | 88 | 97 | 16/min |

FIG. 4A

Wearable Device 2nd Level Database

| Date | Time | Heart Sound |
|---|---|---|
| 12/1/2014 | 9:20AM | Sound1.wav |
| 12/1/2014 | 9:21AM | Sound2.wav |
| 12/1/2014 | 9:22AM | Sound3.wav |
| 12/1/2014 | 9:23AM | Sound4.wav |

FIG. 4B

THRESHOLD DATABASE

| PARAMETER | READING | ACTION |
|---|---|---|
| PULSE | 85 | NONE |
| PULSE | 100 | NONE |
| PULSE | 120 | PLACE TO MEASURE CHEST |
| ... | ... | ... |
| TEMPERATURE | 98 | NONE |
| TEMPERATURE | 100 | PLACE ON FOREHEAD FOR SWEAT |
| TEMPERATURE | 102 | PLACE ON FOREHEAD FOR SWEAT |
| ... | ... | ... |
| RESPIRATORY RATE | 12/MIN | NONE |
| RESPIRATORY RATE | 17/MIN | NONE |
| RESPIRATORY RATE | 23/MIN | PLACE ON CHEST TO MEASURE LUNGS |
| ... | ... | ... |

FIG. 6

METHODS, SYSTEMS, AND WEARABLE APPARATUS FOR OBTAINING MULTIPLE HEALTH PARAMETERS

This application is the U.S. National Phase application under 35 U.S.C. § 371 of International Application No. PCT/EP2016/052214, filed on Feb. 3, 2016, which claims the benefit of Provisional Application Ser. No. 62/111,431, filed Feb. 3, 2015. These applications are hereby incorporated by reference herein.

BACKGROUND

Field of Invention

The present invention generally relates to wearable technology. More specifically, the present invention relates to movable wearable devices that measure health parameters using one or more sensors.

Description of the Related Art

Wearable technology may include any type of mobile electronic device that can be worn on the body, attached to or embedded in clothes and accessories of an individual. Processors and sensors associated with the wearable technology can display, process, or gather information. Such wearable technology has been used in a variety of areas, including monitoring health data of the user as well as other types of data and statistics. These types of devices may be readily available to the public and may be easily purchased by consumers. Examples of some wearable technology in the health arena include the FitBit Flex®, the Nike Fuel Band®, the Jawbone® Up, and the Apple® Watch.

Typically, a wearable device that monitors a health parameter of a user includes a sensor and is designed to be worn around a specific area of the user's body and/or on a particular appendage, such as the user's wrist, upper arm, chest, or waist. Such a wearable device's usefulness is limited in that it cannot measure, or cannot reliably measure, health parameters that are best measured through another part of the user's body near which the wearable is not worn.

SUMMARY OF THE CLAIMED INVENTION

Embodiments of the present invention includes systems and methods directed towards providing a wearable device that can measure health parameters in two levels. The wearable device makes a first measurement of a first health parameter. This is the first "level." The first measurement can then be stored and compared (at the wearable device or elsewhere) to a predetermined health limit stored in a threshold database. If the first measurement exceeds the health limit, the wearable device can then prompt the user to move the wearable device to another part of the user's body to make a second measurement using the first sensor or a second sensor. This is the second "level." The second measurement can measure the first health parameter (e.g., to double-check the first measurement, or to provide a more accurate measurement) or a second health parameter (e.g., to provide additional context for the first measurement, or to measure a possible side effect of a health parameter measured in the first measurement). The wearable device can then transmit the second measurement a user device or to a so-called "levels network," and can receive a message in response.

Generally, in one aspect, a wearable device may include: a housing that is securable to a body of a user adjacent a first position of the body; a power source within the housing; a controller within the housing and operably coupled with the power source; and a first sensor operably coupled with the controller and positioned on or in the housing. The controller may be configured to: obtain, from the first sensor, a first sensor reading indicative of a first health parameter of the user sensed by the first sensor; determine that the first health parameter satisfies a health threshold; in response to the determination, cause the user to be prompted to move the housing to a second position on the user's body; obtain, from the first sensor or from a second sensor, a second sensor reading indicative of the first health parameter or a second health parameter. In various embodiments, the device may include a band coupled with the housing, the band being securable to an appendage of the user.

In various embodiments, the first health parameter is a heart rate. In various embodiments, the second health parameter may be a blood glucose level, a sweat measurement, a respiratory measurement, and/or a body temperature. In various embodiments, the wearable device may include an output device operably coupled with the controller, wherein the controller is further configured to prompt the user to move the housing to the second position via the output device.

In various embodiments, the wearable device may include a wireless communication interface operably coupled with the controller. In various versions, the controller may be further configured to transmit, over the wireless communication interface to a mobile device operated by the user, data indicative of the first sensor reading. In various versions, the controller may be further configured to receive, from a remote computing device via the wireless communication interface, an indication that the first health parameter satisfies the health threshold. In various versions, the controller may be further configured to transmit, over the wireless communication interface to a mobile device operated by the user, data indicative of the second sensor reading. In various versions, the controller is further configured to receive, from a remote computing device via the wireless communication interface, an indication that the second health parameter satisfies another health threshold. In various versions, the wireless communication interface may be a low power Bluetooth interface.

In various embodiments, the health threshold is stored in memory operably coupled with the controller, and the controller is further configured to compare the first health parameter to the health threshold to determine whether the first health parameter satisfies the health threshold. In various embodiments, the controller is further configured to: determine that the second health parameter satisfies another health threshold; and trigger a remedial action in response to the determination that the second health parameter satisfies the another health threshold. In various versions, the remedial action includes one or more of providing audio, visual, or tactile output at an output device operably coupled with the controller, or transmitting, to a remote computing device over a wireless communication interface operably coupled with the controller, an indication that the another health threshold is satisfied. In various versions, the remote computing device may be a computing device operated by a medical professional that is charged with treating the user.

In another aspect, a system may include: one or more processors; a first wireless communication interface operably coupled with the one or more processors; and memory operably coupled with the one or more processors. The memory may store instructions that, when executed by the one or more processors, cause the one or more processors to: receive, over the first wireless communication interface from a wearable device worn at a first position of a body of a user, first data indicative of a first health parameter of the user obtained by the wearable device; determine that the first health parameter satisfies a first health threshold; in response to the determination, cause the user to be prompted to move the wearable device to a second position on the user's body; and receive, over the first wireless communication interface from the wearable device, second data indicative of the first health parameter or a second health parameter of the user obtained by the wearable device at the second position. In various embodiments, the system may include a second wireless communication interface that employs a different wireless technology than the first wireless communication interface.

In yet another aspect, a method may include: receiving, directly or indirectly from a wearable device secured to a first position on a user's body, a first sensor reading indicative of a first health parameter of a user sensed by the wearable device; comparing the first health parameter to one or more health thresholds; in response to a determination that the first health parameter satisfies at least one health threshold, causing the user to be prompted to move the wearable device to a second position on the user's body; and receiving, directly or indirectly from the wearable device, a second sensor reading indicative of the first health parameter or a second health parameter.

BRIEF DESCRIPTION OF THE DRAWINGS

FIG. 3 is a flow diagram illustrating an example operation of the wearable device, including a first-level measurement and a second-level measurement.

FIG. 4A schematically illustrates an example first level database.

FIG. 4B schematically illustrates an example second level database.

FIG. 6 illustrates schematically an example threshold database.

DETAILED DESCRIPTION

Several embodiments of the invention with reference to the appended drawings are now explained. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

Figure 1:
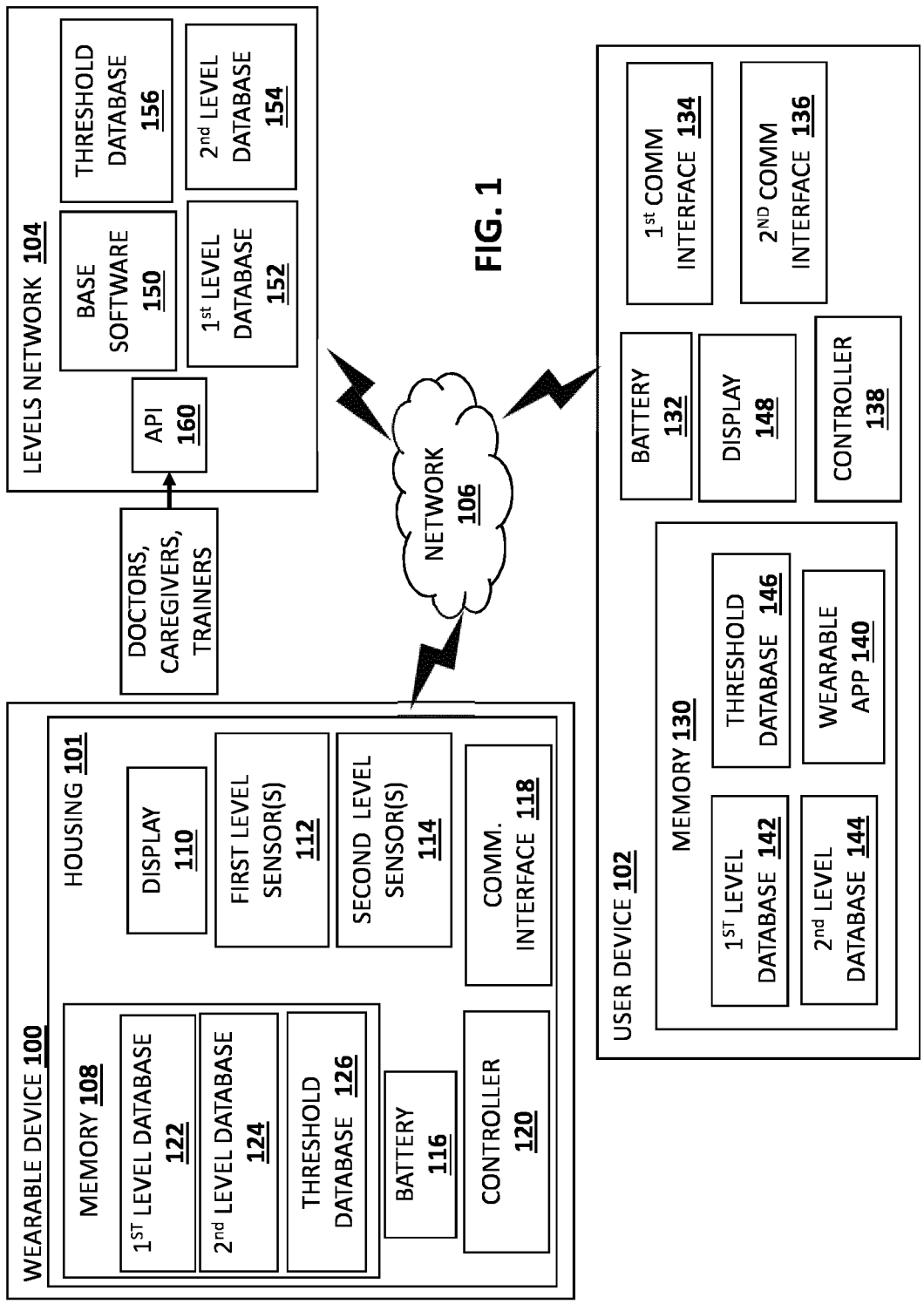
FIG. 1 schematically illustrates an example system of the present invention as described herein.

FIG. 1 illustrates one embodiment of an environment supporting a two level wearable device 100, a user device 102, and a levels network 104. The wearable device 100 and the user device 102 may be connected though one or more wired and/or wireless network connections represented generically by network 106, including but not limited to one or more wireless network connections or near field communication connections. The wearable device 100 and user device 102 may both be connected to the levels network 104 through one or more wired or wireless network connections, also as represented generically by the network 106. In some embodiments, the wearable device 100 may utilize (or "piggyback" on) a wired or wireless network connection of the user device 102 in order to connect to the levels network 104.

The wearable device 100 may include a plurality of components. In some embodiments, these components are all connected to a single bus (e.g., on one or more printed circuit boards) on and/or within a housing 101, though alternatively they could be connected through multiple buses. The plurality of components may include a memory 108, one or more output devices such as a display 110, one or more first level sensors 112, one or more second level sensors 114, a power source such as battery 116, a wired or wireless communication interface 118 (e.g., USB, a Bluetooth low energy module, etc.), and a controller 120. Controller 120 may take various forms, such as one or more processors executing instructions stored in memory 108, a field-programmable gate array ("FPGA"), an application-specific integrated circuit ("ASIC"), and so forth. The memory 108 may store, and the controller 120 of the wearable device 100 may be operable to execute, a wearable device operating system (OS) (not depicted), a wearable device base software (not depicted), a wearable device first level database 122, a wearable device second level database 124, and a wearable device threshold database 126.

In some embodiments, the sensors 112, 114 may include sensors for measuring blood pressure, heart rate, body temperature (e.g., thermometer), blood sugar or glucose, acceleration (e.g., accelerometer), insulin, vitamin levels, respiratory rate, heart sound (e.g., microphone), breathing sound (e.g., microphone), movement speed, steps walked or ran (e.g., pedometer), skin moisture, sweat detection, sweat composition, nerve firings (e.g., electromagnetic sensor), or similar health measurements. In some embodiments, additional sensors may also measure allergens, air quality, air humidity, air temperature, and similar environmental measurements.

The user device 102 of FIG. 1 may include a variety of components as well. In some embodiments, the user device 102 may include a memory 130, a power supply (e.g., a battery 132), a first wired or wireless communication interface 134 (e.g., USB, a Bluetooth low energy module, etc.), a second wireless or wired communication interface 136 (e.g., Wi-Fi, cellular, etc.), and a controller 138. In some embodiments, the memory 130 may be operable to store, and the controller 138 may be operable to execute, a user device operating system (OS, not depicted), a user device two-level wearable software 140 (or "app"), a user device first level database 142, a user device second level database 144, and a user device threshold database 146. In some embodiments, the user device two-level wearable software 140 is operable to communicate with the wearable device 100 or the levels network 104. In some embodiments, the user device 102 may be, for example, a smartphone, a tablet, a laptop computer, a desktop computer, a gaming console, a smart television, a home entertainment system, a second wearable device, or another device that can execute a user interface and store a database. The user device 102 may also include one or more output devices, such as a speaker (not depicted) and/or a display 148 (which may be a touch screen display).

The levels network 104 of FIG. 1 may include a variety of components as well. In some embodiments, the levels network 104 may include or be operable to store and execute an levels network base software 150, a levels network first level database 152, a levels network second level database 154, a levels network threshold database 156, and/or an application program interface ("API") 160 that can be made accessible to third parties (e.g., medical professionals such as doctors or caregivers or trainers or emergency services professionals). The levels network 104 may be hosted on a single server or a collection of networked servers. For example, each of these servers may be one of a structured query language (SQL) server, an index server, a database server, an application server, a gateway server, a broker server, an active directory server, a terminal server, a virtualization services server, a virtualized server, or another machine with similar functionality. These servers may be connected via a wired or wireless connection, e.g., the network 106. In some embodiments, the levels network 104 may also include storage for, or a link or pointer to, a download for the user device two level wearable software 140 that may be made accessible to the user device 102.

The wearable device 100, the user device 102, and the levels network 104 may interact in various ways. For example, the wearable device first level database 122 may be synchronized with the user device first level database 142 and/or the levels network first level database 152, either on its own (through one or more wired or wireless connections such as network 106) or by "piggybacking" on a network connection provided by the user device 102. Similarly, the wearable device second level database 124 may be synchronized with the user device second level database 144 and/or the levels network second level database 154. Similarly, the wearable device threshold database 126 may be synchronized with the user device threshold database 146 and/or the levels network threshold database 156.

According the one embodiment, the wearable device 100 can periodically take a first measurement of a user's first health parameters using one or more of its first level sensors 112. These first level sensors 112 may include a subset of all sensors on the wearable device 100. The time between these first measurements may be, for example, a number of seconds, minutes, hours, or days, and may further be adjusted, for example, through a user interface executed by the wearable device base software or the user device two level wearable software 140. Each first measurement, once measured, may in some embodiments be stored in the wearable device first level database 122. Each first measurement may then be compared to a predefined health threshold in the wearable device threshold database 126 (e.g., as in the "Parameter" and "Reading" columns under the example threshold database of FIG. 5). In some embodiments, the wearable device 100 synchronizes the wearable device threshold database 126 with the user device threshold database 146 and/or the levels network threshold database 156 prior to comparing a first measurement, while in other embodiments, this synchronization may occur after a delay, periodically, upon user input (to the wearable device 100 or to the user device 102) requesting synchronization, or even never. If the health threshold is satisfied, the wearable device 100 may perform an action, which may be defined in the threshold database 126 (e.g., as in the "Action" column of the example threshold database of FIG. 5) or may be preset within the base software of the wearable device 100. In some embodiments, the wearable device first level database 122 only stores first measurements that satisfy a health threshold within the threshold database 126, while in other embodiments, the wearable device first level database 122 stores all first measurements. In some embodiments, the wearable device first level database 122 may be synchronized with the user device first level database 142 and/or the levels network first level database 152 immediately after a first measurement is stored, while in other embodiments this synchronization may occur after a delay, periodically, upon user input (to the wearable device 100 or to the user device 102) requesting synchronization, or never. Once the wearable device 100 determines an action to be taken when the threshold has been satisfied, the wearable device 100 can perform the action, or prompt the user using a display, a vibration, a small electric shock, or a sound played through a speaker of the wearable device 100 and/or the user device 102.

The actions described in the threshold database 126 (or the base software of the wearable device 100) may include prompting the user of the wearable device 100 to move the wearable device 100 to a different position relative to the user's body. The purpose of such an action may be to gather a second sensor measurement that may be, for example, a more detailed measurement, a variation of the same measurement in a different location for redundancy, a variation of the same measurement in a different location to measure a difference in a health parameter across a user's body, or reading from a different sensor to provide context. For example, if a wrist-worn embodiment of the wearable device 100 takes a first measurement of a user's heart rate (using a heart rate sensor) and the first measurement satisfies a threshold stored in the wearable device threshold database 126, the wearable device 100 may take the action of prompting the user (in a manner described previously) to remove the wearable device 100 from his or her wrist and to press it against his or her chest in order to get a recording of the user's heartbeat sound as the second measurement of the wearable device. In the aforementioned example, then, the first measurement is taken using a first sensor (i.e., a heart rate monitor), while the second measurement is taken using a second sensor (i.e., a microphone). In another embodiment, however, the first measurement and the second measurement may be taken using the same sensor; for example, if a first measurement indicates that a user's heart rate satisfies a threshold when measured through a heart rate monitor sensor at the user's wrist, the wearable device 100 may take the action of prompting the user to relocate the wearable device 100 to the user's neck, where the heart rate monitor sensor may take a second measurement observing the heart rate of the user's carotid artery, which might provide a more detailed or accurate measurement of a user's true heart rate, or may simply be used to confirm that the first measurement at the wrist was accurate. As noted previously, the first measurement and the second measurement may be a measurement of any one of blood pressure, heart rate, body temperature (e.g., thermometer), blood sugar or glucose, acceleration e.g., accelerometer), insulin, vitamin levels, respiratory rate, heart sound (e.g., microphone), breathing sound (e.g., microphone), movement speed, steps walked or ran (e.g., pedometer), skin moisture, sweat detection, sweat composition, nerve firings (e.g., electromagnetic sensor), similar health measurements, or any combination thereof.

Once a second measurement is made, it may be stored in the wearable device second level database 124. In some embodiments, the wearable device 100 then initiates a synchronization between the wearable device second level database 124 and the user device second level database 144 and/or the levels network second level database 154. In other embodiments, this synchronization may occur after a delay, periodically, upon user input (to the wearable device 100 or to the user device 102) requesting synchronization, or even never.

Once a second measurement is made, it may also be checked against the wearable device threshold database 126. In some embodiments, as noted before, the wearable device 100 must synchronize the wearable device threshold database 126 with the user device threshold database 146 and/or the levels network threshold database 156 before comparing a second measurement to the wearable device threshold database 126. In some embodiments, the wearable device 100 only trusts the user device threshold database 146, or only trusts the levels network threshold database 156, to be accurate. In others embodiments, this synchronization may occur after a delay, periodically, upon user input (to the wearable device 100 or to the user device 102) requesting synchronization, or even never.

As before with the first measurement, the wearable device threshold database 126 may specify an action to be taken if the second measurement satisfies a certain threshold. For example, this action could be to prompt the user with a message using a display. The action could also be to initiate a vibration, a small electric shock, or a sound played through a speaker of the wearable device 100 and/or user device 102. The action could also be to contact a doctor, caregiver, trainer, or emergency services professional associated with the user, and/or to grant access to (or to send a prompt requesting such persons to access) the levels network first level database 102 and/or the levels network second level database 154, e.g., to through the API 160 to the levels network 104.

Some benefits of a two-level measurement system are prolonging battery life and conserving storage space for the wearable device 100 compared to a device that measures multiple health parameters at all times. For example, heart rate measurements are often used in current-generation wearable devices partly because these measurements do not expend as much battery life as more detailed measurements. A device that records the sound of a user's heartbeat constantly, on the other hand, could conceivably burn through its battery life quickly, and could also conceivably run out of storage space for the heartbeat recordings rather quickly and be forced to delete potentially important heartbeat recordings, possibly endangering the user's life. A two-level measurement system, on the other hand, conserves the battery and storage space of the wearable device 100 so that it may perform a battery-intensive and storage-intensive health parameter measurement only when another sensor measurement indicates that such a measurement may be helpful.

Regarding instances of synchronization discussed above, if a synchronization cannot occur to due to poor connectivity (temporary or permanent) of either the wearable device 100 or user device 102, or due to the levels network 104 being unavailable (temporarily or permanently), the devices in question can perform in a variety of ways. For example, if the levels network 104 is unavailable, the wearable device 100 may synchronize one or more of its databases to the user device database counterparts, and periodically check the availability of the levels network 104 and synchronize with the database counterparts there once the levels network 104 becomes available. In other embodiments, when one device is unavailable to synchronize, synchronization can be entirely disabled for a time. Further, in some embodiments, the wearable device 100 will only check the threshold database 126 and perform an action listed within the threshold database 126 if it has been recently synchronized. If the threshold database 126 has not been synchronized recently due to unavailability of one or more of the other database counterparts (e.g., user device databases 142-146 and levels network databases 152-156), the wearable device 100 may refuse to check the wearable device threshold database 126 and/or perform actions listed in the wearable device threshold database 126. In other embodiments, the wearable device 100 may ignore the fact that the wearable device threshold database 126 has not been recently updated.

In some embodiments, the wearable device threshold database 126 may store not only limits for measurements, but ranges of values that, when exceeded on either side, prompt an action.

Figure 2A:
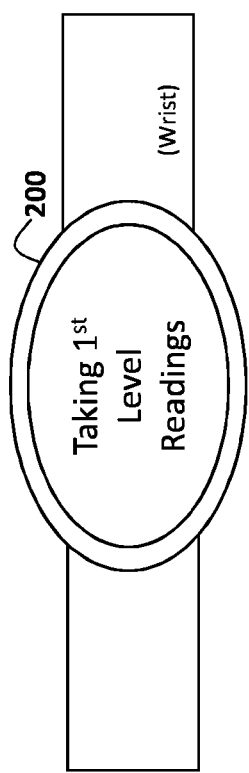
FIG. 2A schematically illustrates an example wearable device that can be worn on a user's wrist, where it takes first-level readings.

FIG. 2A illustrates an example wearable device 200 configured with selected aspects of the present disclosure that can be worn on a user's wrist, where it takes first-level readings. While the example device of FIG. 2A is illustrated as being a wrist-worn device (e.g., a watch or bracelet), this is intended to be an example, rather than a limiting, depiction of the wearable device. The wearable device 200 could be primarily intended to be worn around a user's neck (e.g., a necklace), arm (e.g., an armband), hand (e.g., a glove), neck (e.g., a necklace or scarf), head (e.g., a hat or helmet or headband or headlamp), leg, chest, waist (e.g., a belt), foot (e.g., a shoe or sock), ankle, knee (e.g., a knee brace), or another area of the user's body. The wearable device 200 could also be a device that is primarily intended to be held in a user's hand, or stored in a user's pocket.

Figure 2D:
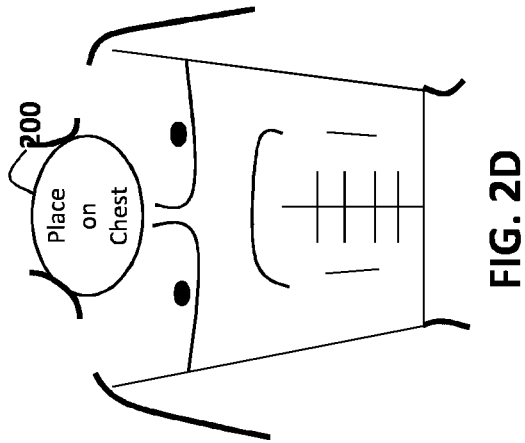
FIG. 2D schematically illustrates an example second-level reading where the wearable device is placed on a user's chest.
Figure 2C:
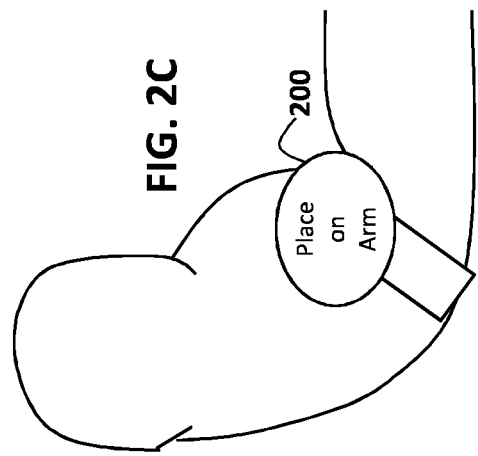
FIG. 2C schematically illustrates an example second-level reading where the wearable device is placed on a user's forearm.
Figure 2B:
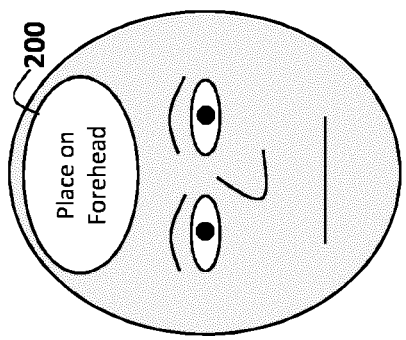
FIG. 2B schematically illustrates an example second-level reading where the wearable device is placed on a user's forehead.

FIG. 2B illustrates an example second-level reading where the wearable device 200 is placed on a user's forehead. In this example, the device of FIG. 2A could, for example, display "place wearable device on forehead" or a similar message to the user if a first measurement satisfies a threshold. The purpose of placing the wearable device 200 on the user's forehead could be, for example, to measure the how much a user is sweating, or the composition of the user's sweat, or to scan how their brain's neurons are firing through an electrode-based or similar system. In one embodiment, the forehead placement of the wearable device 200 as illustrated in FIG. 2B may be the primary "first measurement" level of the wearable device 200, rather than the secondary "second measurement" level of the wearable device 200.

FIG. 2C illustrates an example second-level reading where the wearable device 200 is placed on a user's forearm. In this example, the device of FIG. 2A could, for example, display "place wearable device on forearm" or a similar message to the user if a first measurement satisfies a threshold. The purpose of placing the wearable device 200 on the user's forearm could be, for example, to measure the how much a user is sweating, or the composition of the user's sweat, or to measure forearm muscle movement or gain or deterioration or nerve firings. In one embodiment, the forearm placement of the wearable device 200 as illustrated in FIG. 2C may be the primary "first measurement" level of the wearable device 200, rather than the secondary "second measurement" level of the wearable device 200.

FIG. 2D illustrates an example second-level reading where the wearable device 200 is placed on a user's chest. In this example, the device of FIG. 2A could, for example, display "place wearable device on chest" or a similar message to the user if a first measurement satisfies a threshold. The purpose of placing the wearable device 200 on the user's chest could be, for example, to measure the how much a user is sweating, or the composition of the user's sweat, to measure the user's heart rate, to measure the user's respiratory rate, to record the user's heartbeat sounds, to record the user's breathing sounds, to record the user's coughing sounds, or a similar measurement. In one embodiment, the chest placement of the wearable device 200 as illustrated in FIG. 2D may be the primary "first measurement" level of the wearable device 200, rather than the secondary "second measurement" level of the wearable device 200.

FIG. 3 is a flow diagram illustrating an example operation of the wearable device, including a first-level measurement and a second-level measurement. In this embodiment, the wearable device (e.g., 100, 200) takes a first measurement from a first sensor, and does this periodically—for example, every five minutes, at block 3002. The wearable device stores the data in the wearable device first level database at block 3004. It then checks the wearable device threshold database (e.g., 126) to see if the first measurement satisfies any thresholds at block 3006. If not, then it goes back to block 3002 and takes new first measurement readings according the measurement period (e.g., every five minutes). However, at block 3006, if a first measurement satisfies one or more thresholds in the threshold database, then at block 3008, the wearable device base software checks what action is associated with that threshold and performs that action. In various embodiments, the checking of the threshold database and/or the setting of the action beforehand may be performed on the user device or on the levels network, or on the wearable device itself. The wearable device then performs the action if it can, or at block 3010 displays an action for the user to perform on the display of the wearable device. Once the wearable device has been relocated by the user as per the displayed instructions, the wearable device can initiate the second measurement at block 3012. In one example given in FIG. 2D, this could be measurement of the sound of the user's heartbeat once the user moves the wearable device to his or her chest. The wearable device may then store the second level measurement in the wearable device second level database at block 3014. It may then synchronize the wearable device second level database (and/or the wearable device first level database and/or the wearable device threshold database) with the counterpart databases on the user device and/or the levels network at block 3016.

While the flow diagram in FIG. 3 shows a particular order of operations performed by certain embodiments of the invention, it should be understood that such order is example (e.g., alternative embodiments can perform the operations in a different order, combine certain operations, overlap certain operations, etc.).

FIG. 4A illustrates an example first level database. In this embodiment, the first level database shows the date, the time, and the different parameters that it's always measuring. In this example, it uses: pulse, temperature, and respiratory rate. This example could be a wearable device first level database 122, a user device first level database 142, or a levels network first level database 152. If the three versions of the first level database are synchronized, these should be identical.

FIG. 4B illustrates an example second level database. In this embodiment, the second level database also has the date, the time, and, since it's measuring a more specific parameter—here, heartbeat sound—it stores the file (or a pointer to the file) in the database. As before, this example could be a wearable device second level database 124, a user device second level database 144, or a levels network second level database 154. If the three versions of the second level database are synchronized, these should be identical.

Figure 5:
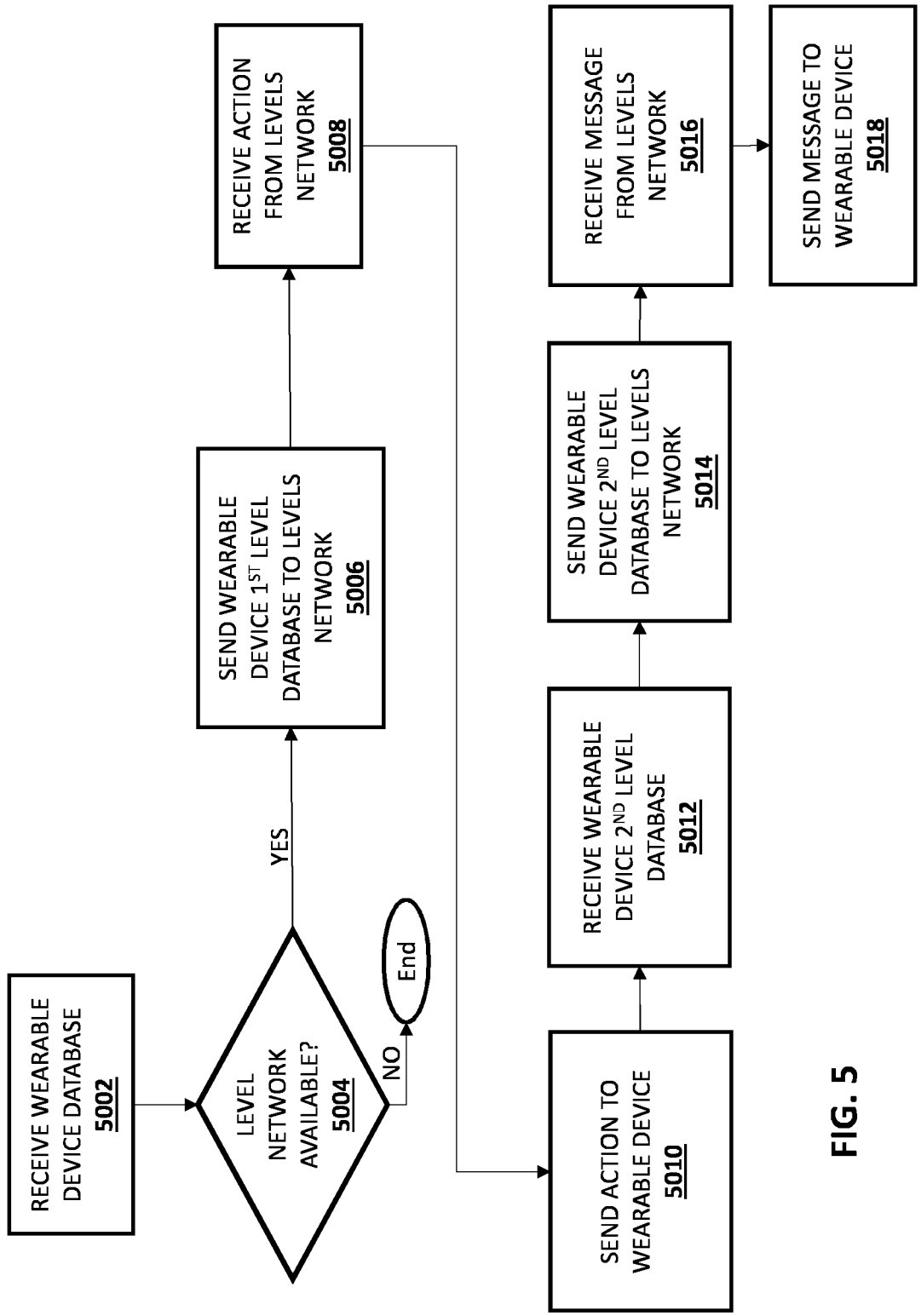
FIG. 5 is a flow diagram illustrating an example operation of the user device, in an embodiment where the user device is responsible for synchronizing the wearable device's data with the levels network.

FIG. 5 is a flow diagram illustrating an example operation of the user device's (e.g., 102) two level wearable software, in an embodiment where the user device is responsible for synchronizing the wearable device's data with the levels network. In this embodiment, the user device begins its process at block 5002 by receiving the wearable device's first level database. In this embodiment, the threshold "decision" is made on the level network (e.g., 104), meaning that the wearable device and user device trust only the threshold database on the level network. One reason for this might be that, because doctors/caregivers/trainers have access to the API (e.g., 160) for the levels network threshold database (e.g., 156), these individuals are able to update these limits according to their professional opinions. In such a situation, an out-of-date threshold database could enforce, for example, a doctor's opinion that is no longer valid. In other embodiments, the wearable device and/or user device may "trust" other threshold databases.

Carrying on with the embodiment of FIG. 5, if decision is to be made on the levels network, then the user device (or wearable device) may check that the levels network's databases are available at block 5004. If the answer is no, then in this embodiment, the process may end without synchronization or checking of limits. However, if the levels network is available, the wearable device first level database may be synchronized to the levels network first level database at block 5006. In some embodiments, this may entail the user device 102 allowing the wearable device to "piggyback" its network connection (e.g., file transfer from the wearable device to the user device through Bluetooth, and file transfer from the user device to the levels network through a Wi-Fi/3G/4G/LTE network connection). In another embodiment, this synchronization may be done through the wearable device's own Wi-Fi/3G/4G/LTE network connection. In either case, in the embodiment of FIG. 5, the user device (and/or wearable device) then receives actions (a.k.a. "action messages") from the level network at block 5008.

In some embodiments, at block 5010, the user device may send an action message to the wearable device, such as "move sensor to chest." At block 5012, the user device may receive, e.g., from the wearable device over a Bluetooth connection, a second level database including the second level reading obtained by the wearable device. At block 5014, the user device may send (e.g., forward) the second level database to the levels network. At block 5016, the user device may receive, e.g., from the levels network, a message (e.g., "Get medical help immediately, "take insulin promptly", etc.). At block 5018, the user device may send (e.g., forward) this message to the wearable device, e.g., so that the wearable device may output the message for consumption by the user.

While the flow diagram in FIG. 5 shows a particular order of operations performed by certain embodiments of the invention, it should be understood that such order is example (e.g., alternative embodiments can perform the operations in a different order, combine certain operations, overlap certain operations, etc.).

FIG. 6 is an example threshold database. It shows a health parameter ("Parameter"), a measurement limit ("Reading"), and an action that should be taken if a current measurement reaches the given measurement limit ("Action"). For example, the threshold database may use pulse (heart rate) as a parameter. As illustrated, the readings go from 85 to 100 to 120. The actions vary—none if it's 85, none if it's 100, but at 120, a user's pulse would be considered too high to be a healthy resting heart rate, so an action is given to query the user to place the wearable device on his or her chest to measure his or her heartbeat sounds.

Another example of a health parameter that can be placed in the threshold database is temperature. The first reading in the threshold database is 95 degrees F.; no action is given. However, temperature—when the reading meets or exceeds 100 degrees F., the threshold database indicates that the user should place the wearable device on his or her forehead to measure sweat.

And the last example health parameter in this example threshold database is the respiratory rate. One given measurement is twelve breaths per minute—which demands no action—because that may be considered within healthy ranges. The next respiratory rate is seventeen breaths per minute—still no action taken. The next respiratory rate is twenty-three breaths per minute, which may be too high to be considered a resting state, in which case the threshold database indicates that the wearable device should prompt the user to place the wearable device on his or her chest to measure the sound of the user's lungs, for example.

Figure 7:
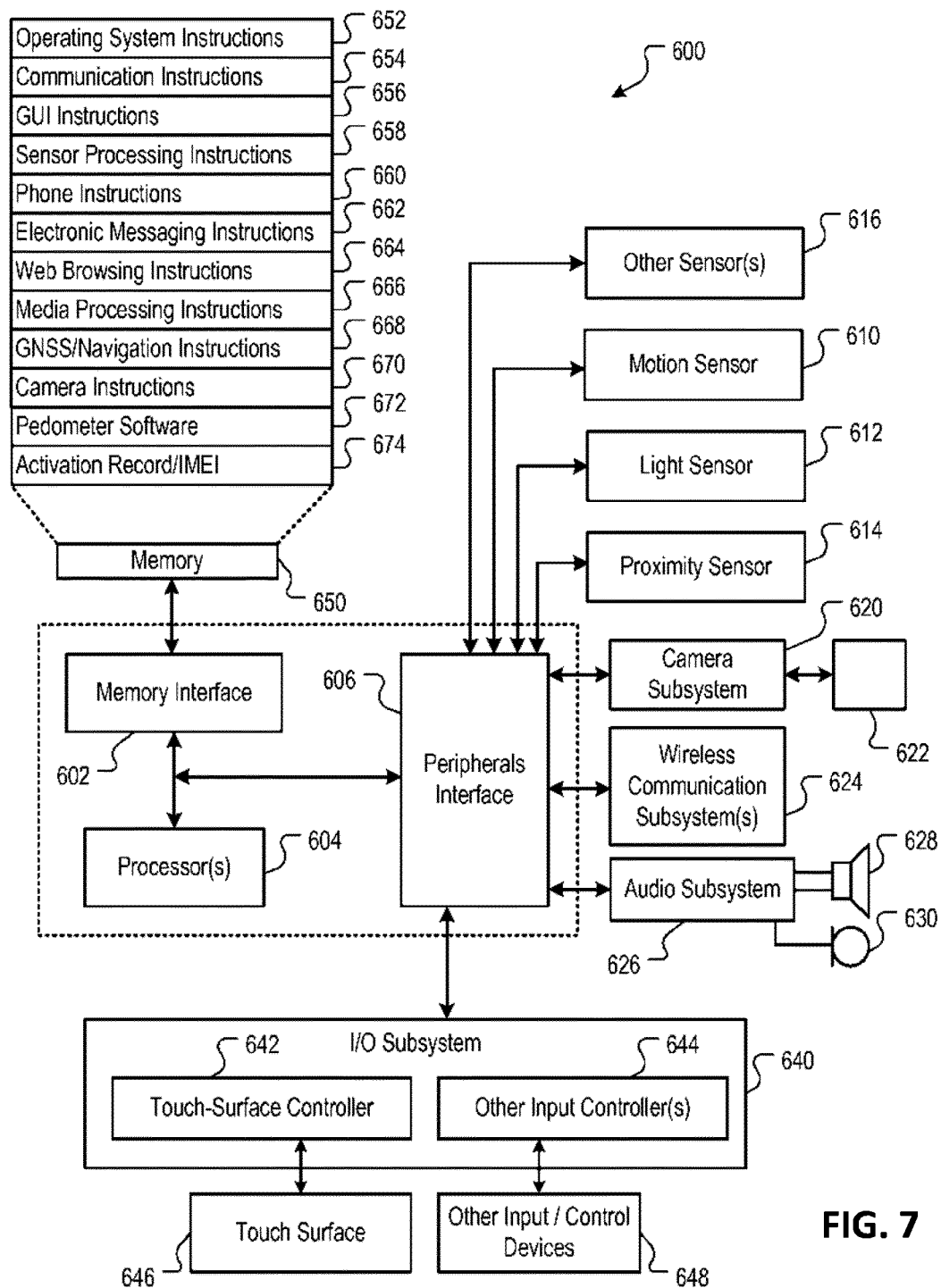
FIG. 7 illustrates an example computing device architecture that may be utilized to implement the various features and processes described herein.

FIG. 7 illustrates an example computing device architecture that may be utilized to implement the various features and processes described herein. For example, the computing device architecture 600 could be implemented in the wearable device or the user device. Architecture 600 as illustrated in FIG. 7 includes memory interface 602, processors 604, and peripheral interface 606. Memory interface 602, processors 604 and peripherals interface 606 can be separate components or can be integrated as a part of one or more integrated circuits. The various components can be coupled by one or more communication buses or signal lines.

Processors 604 as illustrated in FIG. 7 is meant to be inclusive of data processors, image processors, central processing unit, or any variety of multi-core processing devices. Any variety of sensors, external devices, and external subsystems can be coupled to peripherals interface 606 to facilitate any number of functionalities within the architecture 600 of the exemplar mobile device. For example, motion sensor 610, light sensor 612, and proximity sensor 614 can be coupled to peripherals interface 606 to facilitate orientation, lighting, and proximity functions of the mobile device. For example, light sensor 612 could be utilized to facilitate adjusting the brightness of touch surface 646. Motion sensor 610, which could be exemplified in the context of an accelerometer or gyroscope, could be utilized to detect movement and orientation of the mobile device. Display objects or media could then be presented according to a detected orientation (e.g., portrait or landscape).

Other sensors could be coupled to peripherals interface 606, such as a temperature sensor, a biometric sensor, or other sensing device to facilitate corresponding functionalities. Location processor 615 (e.g., a global positioning transceiver) can be coupled to peripherals interface 606 to allow for generation of geo-location data thereby facilitating geo-positioning. An electronic magnetometer 616 such as an integrated circuit chip could in turn be connected to peripherals interface 606 to provide data related to the direction of true magnetic North whereby the mobile device could enjoy compass or directional functionality. Camera subsystem 620 and an optical sensor 622 such as a charged coupled device (CCD) or a complementary metal-oxide semiconductor (CMOS) optical sensor can facilitate camera functions such as recording photographs and video clips.

Communication functionality can be facilitated through one or more communication subsystems 624, which may include one or more wireless communication subsystems. Wireless communication subsystems 624 can include 802.*x* or Bluetooth transceivers as well as optical transceivers such as infrared. Wired communication system can include a port device such as a Universal Serial Bus (USB) port or some other wired port connection that can be used to establish a wired coupling to other computing devices such as network access devices, personal computers, printers, displays, or other processing devices capable of receiving or transmitting data. The specific design and implementation of communication subsystem 624 may depend on the communication network or medium over which the device is intended to operate. For example, a device may include wireless communication subsystem designed to operate over a global system for mobile communications (GSM) network, a GPRS network, an enhanced data GSM environment (EDGE) network, 802.x communication networks, code division multiple access (CDMA) networks, or Bluetooth networks. Communication subsystem 624 may include hosting protocols such that the device may be configured as a base station for other wireless devices. Communication subsystems can also allow the device to synchronize with a host device using one or more protocols such as TCP/IP, HTTP, or UDP.

Audio subsystem 626 can be coupled to a speaker 628 and one or more microphones 630 to facilitate voice-enabled functions. These functions might include voice recognition, voice replication, or digital recording. Audio subsystem 626 in conjunction may also encompass traditional telephony functions.

I/O subsystem 640 may include touch controller 642 and/or other input controller(s) 644. Touch controller 642 can be coupled to a touch surface 646. Touch surface 646 and touch controller 642 may detect contact and movement or break thereof using any of a number of touch sensitivity technologies, including but not limited to capacitive, resistive, infrared, or surface acoustic wave technologies. Other proximity sensor arrays or elements for determining one or more points of contact with touch surface 646 may likewise be utilized. In one implementation, touch surface 646 can display virtual or soft buttons and a virtual keyboard, which can be used as an input/output device by the user.

Other input controllers 644 can be coupled to other input/control devices 648 such as one or more buttons, rocker switches, thumb-wheels, infrared ports, USB ports, and/or a pointer device such as a stylus. The one or more buttons (not shown) can include an up/down button for volume control of speaker 628 and/or microphone 630. In some implementations, device 600 can include the functionality of an audio and/or video playback or recording device and may include a pin connector for tethering to other devices.

Memory interface 602 can be coupled to memory 650. Memory 650 can include high-speed random access memory or non-volatile memory such as magnetic disk storage devices, optical storage devices, or flash memory. Memory 650 can store operating system 652, such as Darwin, RTXC, LINUX, UNIX, OS X, ANDROID, WINDOWS, or an embedded operating system such as VxWorks. Operating system 652 may include instructions for handling basic system services and for performing hardware dependent tasks. In some implementations, operating system 652 can include a kernel.

Memory 650 may also store communication instructions 654 to facilitate communicating with other mobile computing devices or servers. Communication instructions 654 can also be used to select an operational mode or communication medium for use by the device based on a geographic location, which could be obtained by the GPS/Navigation instructions 668. Memory 650 may include graphical user interface instructions 656 to facilitate graphic user interface processing such as the generation of an interface; sensor processing instructions 658 to facilitate sensor-related processing and functions; phone instructions 660 to facilitate phone-related processes and functions; electronic messaging instructions 662 to facilitate electronic-messaging related processes and functions; web browsing instructions 664 to facilitate web browsing-related processes and functions; media processing instructions 666 to facilitate media processing-related processes and functions; GPS/Navigation instructions 668 to facilitate GPS and navigation-related processes, camera instructions 670 to facilitate camera-related processes and functions; pedometer software 672, activation record/IMEI 674; and instructions for any other application that may be operating on or in conjunction with the mobile computing device. Memory 650 may also store other software instructions for facilitating other processes, features and applications, such as applications related to navigation, social networking, location-based services or map displays.

Each of the above identified instructions and applications can correspond to a set of instructions for performing one or more functions described above. These instructions need not be implemented as separate software programs, procedures, or modules. Memory 650 can include additional or fewer instructions. Furthermore, various functions of the mobile device may be implemented in hardware and/or in software, including in one or more signal processing and/or application specific integrated circuits.

Certain features may be implemented in a computer system that includes a back-end component, such as a data server, that includes a middleware component, such as an application server or an Internet server, or that includes a front-end component, such as a client computer having a graphical user interface or an Internet browser, or any combination of the foregoing. The components of the system can be connected by any form or medium of digital data communication such as a communication network. Some examples of communication networks include LAN, WAN and the computers and networks forming the Internet. The computer system can include clients and servers. A client and server are generally remote from each other and typically interact through a network. The relationship of client and server arises by virtue of computer programs running on the respective computers and having a client-server relationship to each other.

One or more features or steps of the disclosed embodiments may be implemented using an API that can define on or more parameters that are passed between a calling application and other software code such as an operating system, library routine, function that provides a service, that provides data, or that performs an operation or a computation. The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer will employ to access functions supporting the API. In some implementations, an API call can report to an application the capabilities of a device running the application, such as input capability, output capability, processing capability, power capability, and communications capability.

Figure 8:
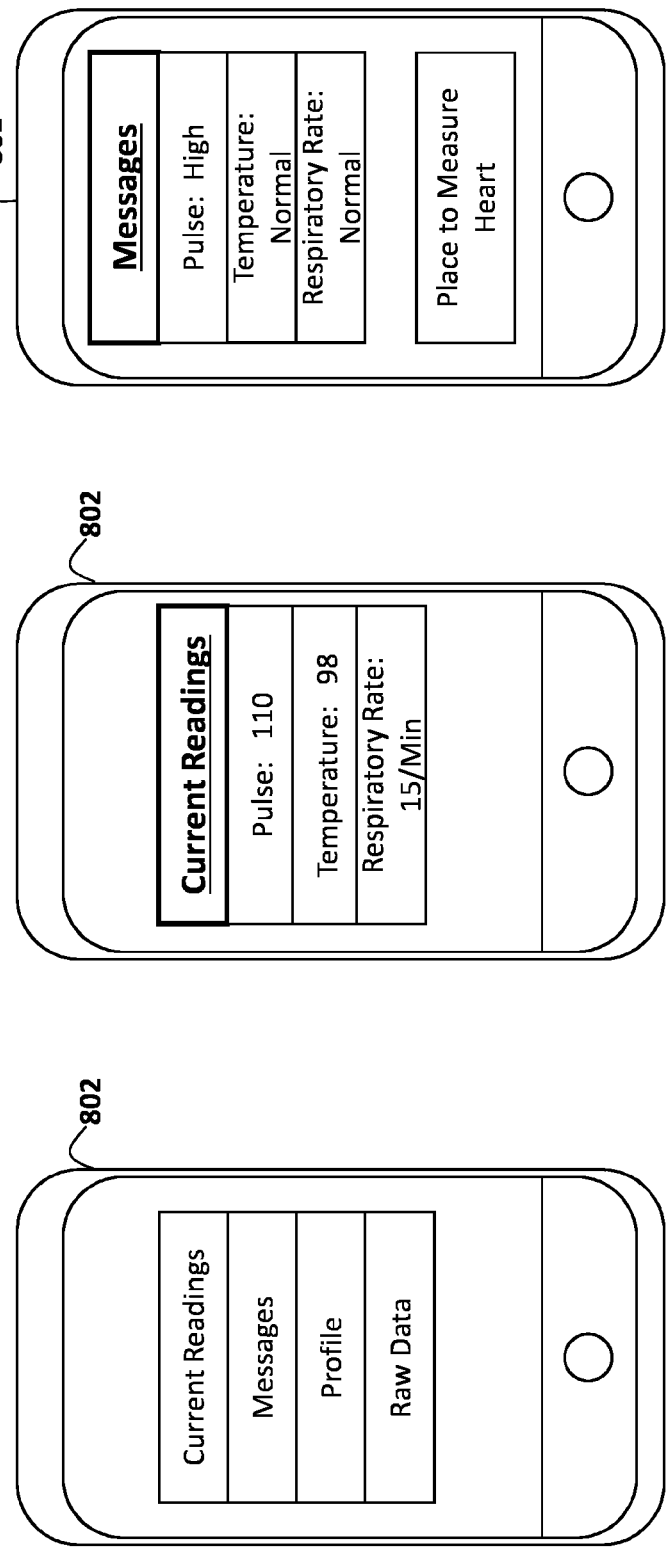
FIG. 8A is an illustration an example menu interface that can be displayed by the user device.
FIG. 8B is an illustration an example readings interface that can be displayed by the user device.
FIG. 8C is an illustration an example messages interface that can be displayed by the user device.

FIGS. 8A, B, and C illustrate an example menu interface that can be displayed by the user device 802 (which may be configured similarly as, for instance, user device 102 of FIG. 1) while it is executing the two level wearable software. FIG. 8A shows a user device menu that allows a user to select between viewing the user's current sensor measurements ("Current readings"), the user's messages ("messages"), the user's profile ("profile") (to change some personal information, for example), and the user's raw data ("raw data") if they would like to see that.

FIG. 8B is an illustration an example readings interface that can be displayed by the user device while it is executing the two level wearable software. This is an example screen of the two level wearable software after a user taps "current readings" in the menu of FIG. 8A. It shows, for example, the user's pulse—here, approximately 110; and temperature—here, approximately 98; and respiratory rate—here, approximately 15 breaths per minute.

FIG. 8C is an illustration an example messages interface that can be displayed by the user device while it is executing the two level wearable software. This is an example screen of the two level wearable software after a user taps "messages" in the menu of FIG. 8A. FIG. 8C shows the messages that the user has received from the levels network. It shows, for example, that the user's pulse is high, the user's temperature is normal, and the user's respiratory rate is normal. The example screen also shows another message from the levels network "place to measure heart"—indicating that the user should place the wearable device on his or her chest in order to take a heartbeat sound measurement, for example.

Figure 9:
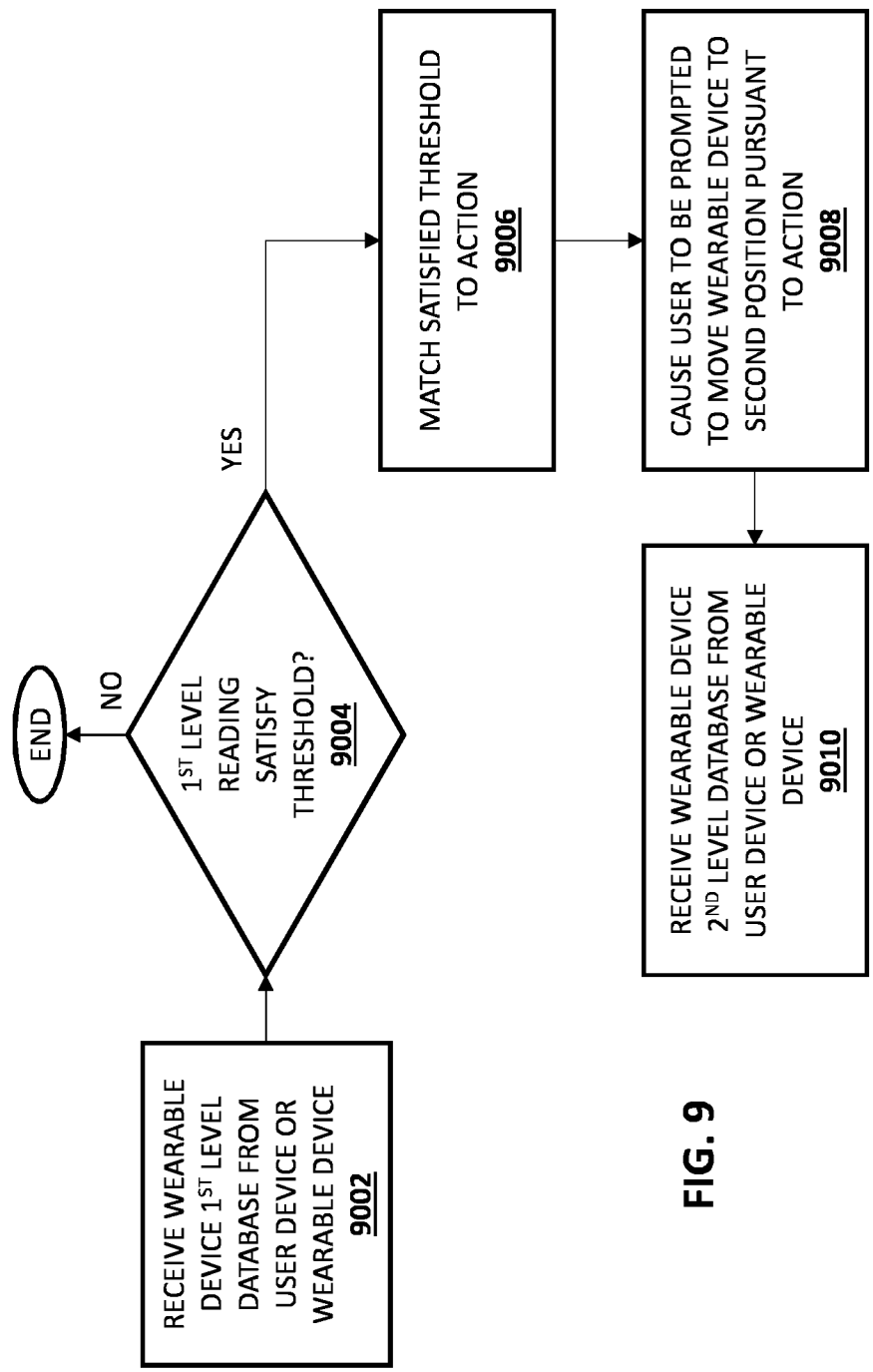
FIG. 9 is a flow diagram illustrating an example operation of the levels network, including a first-level measurement and a second-level measurement.

FIG. 9 is a flow diagram illustrating an example operation of the levels network's base software, including a first-level measurement and a second-level measurement. The levels network base software first receives, directly or indirectly from the wearable device at block 9002, the first level database. In some embodiments, the first level database may be transmitted indirectly from the wearable device to the levels network's first level database via the user device. In other embodiments (e.g., where the wearable device has a Wi-Fi or cellular interface), the first level database may be transmitted directly to the levels network by the wearable device. The levels network's threshold database may then be compared to the measurement from the first level database at block 9004 to determine whether any health thresholds are satisfied. If the answer at block 9004 is no, then the method may end.

But if the answer at block 9004 is yes, then at block 9006, the levels network may match one or more action to the one or more satisfied thresholds. For example, if a heart rate satisfies a hypertension threshold, then a matching action may be to cause the user to be prompted to place the wearable device at a location such as the user's neck to obtain a more accurate heart rate reading. As another example, suppose a body temperature measured by a wearable device worn on a user's wrist satisfies a fever threshold. A matching action may be to cause the user to be prompted to place the wearable device at a location suitable to obtain a more accurate body temperature measurement, such as on the user's forehead and/or in the user's armpit, or at a location suitable to obtain a measurement of another fever symptom, such as the user's forehead to obtain a sweat measurement.

At block 9008, in accordance with the one or more matching actions, the user may be prompted to move the wearable device to a second position on the user's body to obtain a second sensor reading. In some embodiments, the levels network may transmit a message directly or indirectly (e.g., through the user device) to the wearable device to cause the wearable device to prompt the user. In some embodiments, the levels network may transmit a message to the user device to cause the user device to provide output (e.g., audible, visual, tactile) prompting the user to move the wearable device. At block 9010, the levels network may receive a second sensor reading directly or indirectly (e.g., through the user device) from the wearable device.

While the flow diagram in FIG. 9 shows a particular order of operations performed by certain embodiments of the invention, it should be understood that such order is example (e.g., alternative embodiments can perform the operations in a different order, combine certain operations, overlap certain operations, etc.).

Figure 10:
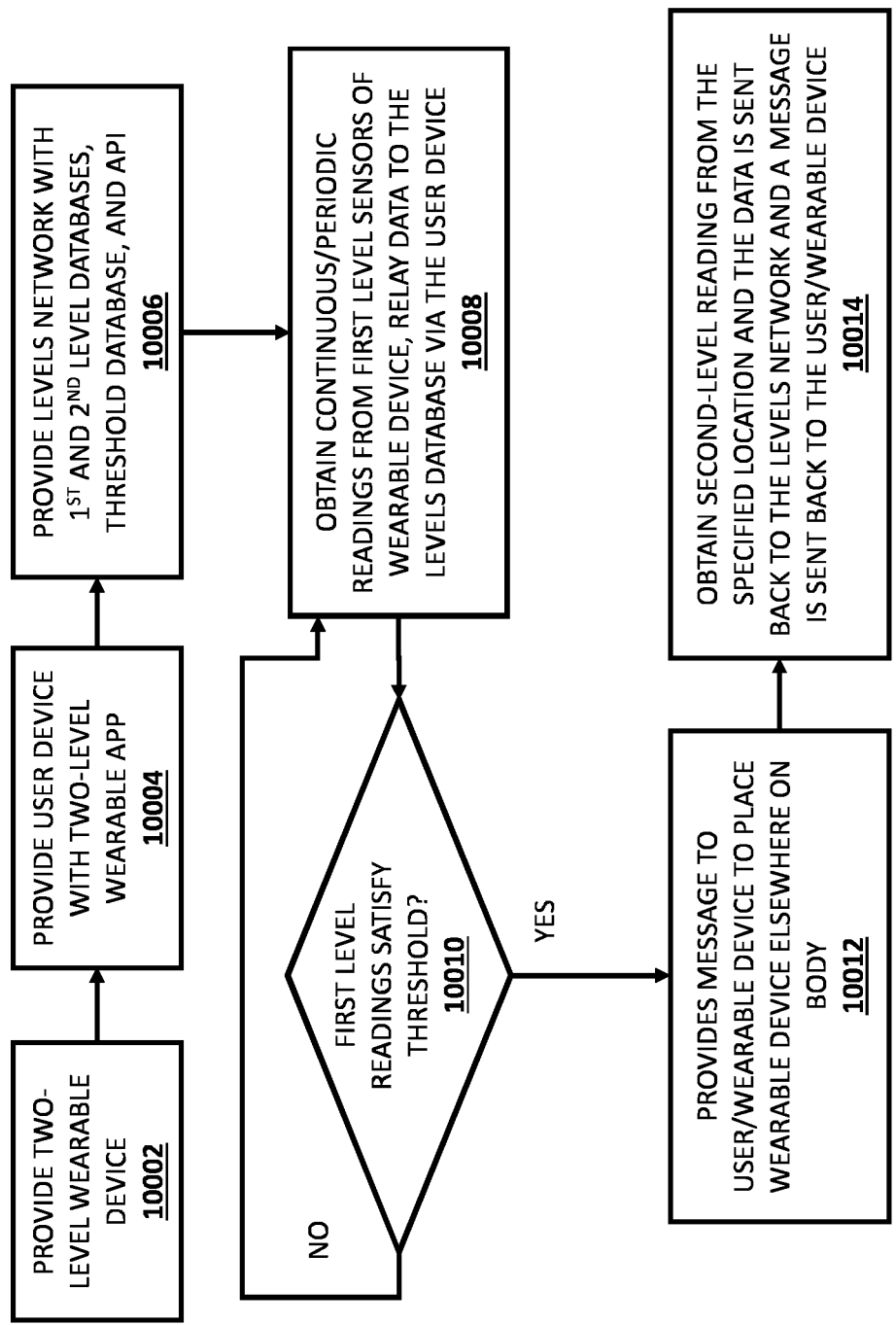
FIG. 10 illustrates an example overall method of the present invention as described herein.

FIG. 10 illustrates an example overall method of the present invention as described herein. This overall method provides for the two level wearable device described above, the user device described above, and the levels network described above. The overall method describes the execution of continuous (or periodic) first readings ("base readings") from the first sensors in the wearable device. At block 10002, a two-level wearable device configured with selected aspects of the present disclosure, e.g., through software installed on the wearable device, may be provided. The wearable device may include, as described above, first and second level databases (e.g., 122 and 124 in FIG. 1), first and/or second level sensors (e.g., 112 and 114 in FIG. 1), and/or a threshold database (e.g., 126 in FIG. 1).

At block 10004, a user device such as a smart phone, tablet, etc., may be provided with a two-level wearable app (e.g., 140 in FIG. 1). Accompanying the two-level wearable app, e.g., in memory 130 of user device 102, may be a first and second level databases (e.g., 142 and 144 in FIG. 1), and a threshold database (e.g., 146 in FIG. 1). At block 10006, a levels network may be provided with first and second levels databases (e.g., 152 and 154 in FIG. 1), a threshold database (e.g., 156 from FIG. 1), and an API (e.g., 160 in FIG. 1).

At block 10008, the wearable device may, continuously and/or periodically, obtain first level readings using the first level sensor. At block 10010, a determination may be made, e.g., at the wearable device, at the user device, or on the levels network, of whether the first level readings satisfy one or more health thresholds. If the answer is no, then method 10000 may proceed back to block 10008. However, if the answer at block 10010 is yes, then method may proceed to block 10012.

At block 10012, a message may be provided to the user, e.g., as output from the wearable device or from the user device, to place the wearable device elsewhere on the user's body to obtain one or more second-level sensor readings. Examples of this are described above and shown in FIGS. 2B-D. Once the wearable device is repositioned on the user's body as instructed, at block 10014, one or more second level readings may be obtained by the wearable device from one or more sensors. Data indicative of the readings may be sent directly or indirectly (e.g., via the user device) to the levels network. In response, a message may be sent back to the user device and/or the wearable device to take some remedial action (e.g., "call 911," "decrease sodium intake," "take insulin," "rest," etc.).

While the flow diagram in FIG. 10 shows a particular order of operations performed by certain embodiments of the invention, it should be understood that such order is example (e.g., alternative embodiments can perform the operations in a different order, combine certain operations, overlap certain operations, etc.).

Embodiments of the invention also relate to an apparatus for performing the operations herein. Such a computer program is stored in a non-transitory computer-readable medium. A machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures can be performed by processing logic that comprises hardware (e.g. circuitry, dedicated logic, etc.), software (e.g., embodied on a non-transitory computer readable medium), or a combination of both. Although the processes or methods are described above in terms of some sequential operations, it should be appreciated that some of the operations described can be performed in a different order. Moreover, some operations can be performed in parallel rather than sequentially.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claims.

What is claimed is:

1. A wearable device, comprising:
a housing that is securable to a body of a user adjacent a first position of the body;
a power source within the housing;
a controller within the housing and operably coupled with the power source; and
a first sensor operably coupled with the controller and positioned on or in the housing;
wherein the controller is configured to:
obtain, from the first sensor, a first sensor reading indicative of a first health parameter of the user sensed by the first sensor;
determine that the first health parameter exceeds a health threshold or receive an indication from a separate device that the first health parameter exceeds the health threshold;
in response to the determination or the receipt of the indication, prompt the user or a medical professional to move the housing to a second position on the user's body; and
obtain, from the first sensor or from a second sensor, a second sensor reading indicative of a second health parameter different from the first health parameter after the housing is moved to the second position to provide additional context for the first sensor reading.

2. The wearable device of claim 1, wherein the first health parameter is a heart rate.

3. The wearable device of claim 2, wherein the second health parameter is a blood glucose level.

4. The wearable device of claim 2, wherein the second health parameter is at least one of a sweat measurement and a respiratory measurement.

5. The wearable device of claim 2, wherein the second health parameter is a body temperature.

6. The wearable device of claim 1, further comprising a band coupled with the housing, the band being securable to an appendage of the user.

7. The wearable device of claim 1, further comprising an output device operably coupled with the controller and configured to prompt the user or the medical professional to move the housing to the second position.

8. The wearable device of claim 1, further comprising a wireless communication interface operably coupled with the controller.

9. The wearable device of claim 8, wherein the controller is further configured to transmit, over the wireless communication interface to a mobile device operated by the user, data indicative of the first sensor reading.

10. The wearable device of claim 8, wherein the controller is further configured to receive, from a remote computing device via the wireless communication interface, the indication that the first health parameter exceeds the health threshold.

11. The wearable device of claim 8, wherein the controller is further configured to transmit, over the wireless communication interface to a mobile device operated by the user, data indicative of the second sensor reading.

12. The wearable device of claim 11, wherein the controller is further configured to receive, from a remote computing device via the wireless communication interface, an indication that the second health parameter satisfies another health threshold.

13. The wearable device of claim 8, wherein the wireless communication interface comprises a Bluetooth low energy interface.

14. The wearable device of claim 1, wherein the health threshold is stored in memory operably coupled with the controller, and the controller is further configured to compare the first health parameter to the health threshold to determine whether the first health parameter exceeds the health threshold.

15. A computer-implemented method, comprising:
receiving, by one or more processors directly or indirectly from a wearable device secured to a first position on a user's body, a first sensor reading indicative of a first health parameter of the user sensed by the wearable device;
comparing, by the one or more processors, the first health parameter to one or more health thresholds;
determining that the first health parameter exceeds the one or more health thresholds;
in response to the determining that the first health parameter exceeds the one or more health thresholds, prompting, by the one or more processors, the user or a medical professional to move the wearable device to a second position on the user's body; and
receiving, by the one or more processors directly or indirectly from the wearable device, a second sensor reading indicative of the first health parameter or a second health parameter after the wearable device is moved to the second position to provide additional context for the first sensor reading.

* * * * *